United States Patent
Bales et al.

(10) Patent No.: US 11,344,343 B2
(45) Date of Patent: May 31, 2022

(54) CANNULATED COMPRESSION DEVICE

(71) Applicant: Ideas In Surgery, Inc., Tampa, FL (US)

(72) Inventors: Joel Bales, Tampa, FL (US); Kyle W. Schweser, Columbia, MO (US)

( * ) Notice: Subject to any disclaimer, the term of this patent is extended or adjusted under 35 U.S.C. 154(b) by 179 days.

(21) Appl. No.: 16/852,817

(22) Filed: Apr. 20, 2020

(65) Prior Publication Data
US 2021/0322069 A1    Oct. 21, 2021

(51) Int. Cl.
*A61B 17/72* (2006.01)
*A61B 17/86* (2006.01)

(52) U.S. Cl.
CPC ........ *A61B 17/7225* (2013.01); *A61B 17/864* (2013.01); *A61B 17/8665* (2013.01)

(58) Field of Classification Search
CPC .............. A61B 17/7225; A61B 17/864; A61B 17/8665
USPC .. 606/62, 63, 65, 66, 67, 68, 301, 305, 310, 606/312, 315, 320
See application file for complete search history.

(56) References Cited

U.S. PATENT DOCUMENTS

| | | | | |
|---|---|---|---|---|
| 2002/0161369 A1* | 10/2002 | Bramlet | ............ | A61B 17/7266 606/67 |
| 2005/0177158 A1* | 8/2005 | Doubler | ............ | A61B 17/7225 606/64 |
| 2013/0274747 A1* | 10/2013 | Fagan | ................ | A61B 17/7266 606/64 |
| 2016/0287301 A1* | 10/2016 | Mehl | ..................... | A61B 17/863 |
| 2018/0071000 A1* | 3/2018 | Pham | ................ | A61B 17/8685 |
| 2019/0008570 A1* | 1/2019 | Rowe | ..................... | A61B 17/68 |

* cited by examiner

*Primary Examiner* — Eduardo C Robert
*Assistant Examiner* — David C Comstock
(74) *Attorney, Agent, or Firm* — Larson & Larson, P.A.; Justin P. Miller; Frank Liebenow (57) ABSTRACT

The cannulated compression device creates fixation and compression across its tang housing, thus stabilizing and closing a bone fracture during placement. After insertion of the cannulated compression device, tangs are extended outward from the tang housing, locking the tang housing with respect to both rotational and axial movement. A compression nut is then threaded onto the proximal end of the tang housing. The nut has two sets of threads: a first set of threads interfaces with the tang housing, a second set of threads interfaces with the bone. By using different pitches, the amount of linear movement for the first set of threads and second set of threads is different.

12 Claims, 11 Drawing Sheets

CANNULATED COMPRESSION DEVICE

FIELD

This invention relates to the field of bone implants and more particularly to a device that compresses fractures during placement.

BACKGROUND

Bone screws have long been used to fix bone fragments in place. As with most screws, bone screws are formed from an inclined plane, or thread, that encircles a cylinder. The resulting mechanism converts rotational motion into linear motion.

A head on the screw creates a bearing surface that presses against the upper surface of the bone. The head also creates space for a tool interface.

But the rotation of a screw can cause problems during placement, such as rotating the underlying bone during the process of driving the screw into place.

What is needed is a device that will avoid rotation during placement, but still compress a bone fracture.

SUMMARY

The cannulated compression device creates fixation and compression across its tang housing, thus stabilizing and closing a bone fracture during placement.

After insertion of the cannulated compression device, tangs are extended outward from the tang housing, locking the tang housing with respect to both rotational and axial movement.

A compression nut is then threaded onto the proximal end of the tang housing. The nut has two sets of threads: a first set of threads that interfaces with the tang housing, a second set of threads that interfaces with the bone.

By using different threads, the amount of linear movement for the first set of threads and second set of threads is different. Threads may differ in pitch or in lead arrangement.

Regarding pitch, pitch is the distance from the crest of one thread to the next. A larger thread pitch means a greater length between threads, thus more linear movement for a single rotation.

Regarding leads, a nut may advance one thread at a time, which is conventional, or more than one at a time. For example, by two threads per rotation in double-start or double-lead arrangement.

The benefit of a double-lead arrangement is that the linear speed of motion of the nut is increased, given that two threads are advanced with every turn. As an added benefit, the load is spread across at least two threads, thus increasing the load that can be sustained prior to deformation.

In a first embodiment, the first set of threads, connecting the compression nut to the tang housing of the device, has a greater pitch than the second set of threads, connecting the compression nut to the hole in the bone.

Thus, a single rotation of the compression nut results in more linear movement with respect to the tang housing than with respect to the bone, thus pulling the device toward the compression nut and compressing any intervening fracture.

In a second embodiment, the first set of threads, connecting the compression nut to the tang housing of the device, has a lesser pitch than the second set of threads that connects the compression nut to the hole in the bone. But the first set of threads is double-lead or triple-lead, thus doubling or tripling, respectively, the linear movement of the threads for a single turn.

Thus, a single rotation of the compression nut results in more linear movement with respect to the tang housing than with respect to the bone, thus pulling the device toward the compression nut and compressing any intervening fracture.

The steps of placing the device are as follows:

A guide wire is passed to guide placement;

A hole is drilled in the bone over the guide wire;

The device is passed over guide wire, using the insertion tool to provide downward force until the device is seated at the correct depth;

The tang extension tool is passed through the insertion tool, threading through the hubs of the tangs. Rotation of the tang extension tool extends the tangs the desired amount;

The tang extension tool is removed, the insertion tool is removed, the compression sleeve is threaded onto the compression nut, and the insertion tool is again placed;

The compression nut driver is then passed through the insertion tool and compression sleeve, interfacing with the compression nut;

Rotation of the compression nut driver rotates the compression nut, the compression nut then moves toward the tangs of the device and through the hole into the bone;

Initially the threads of the compression nut have not entered the bone, thus the need for the compression sleeve to create an interface for the external threads of the compression nut to pass;

As the compression nut threads into the bone, the nut draws the device toward the tangs, closing any gap in the fracture;

When the compression nut is fully driven into the bone, placement is complete, and the tools are removed.

The device is left in place to fix the bone fracture, and the bone heals around the device.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
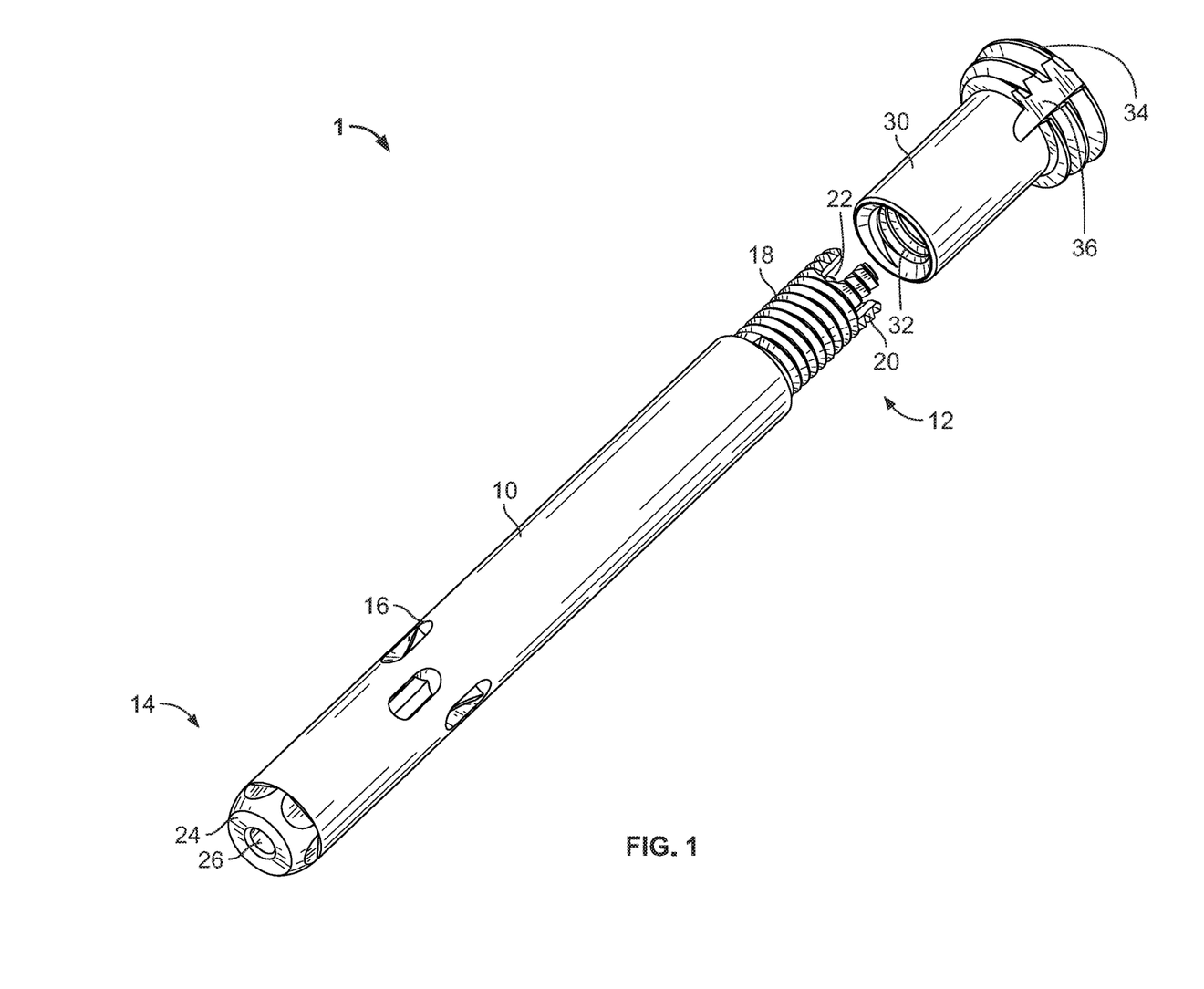
FIG. 1 illustrates a first isometric view of the cannulated compression device.
Figure 2:
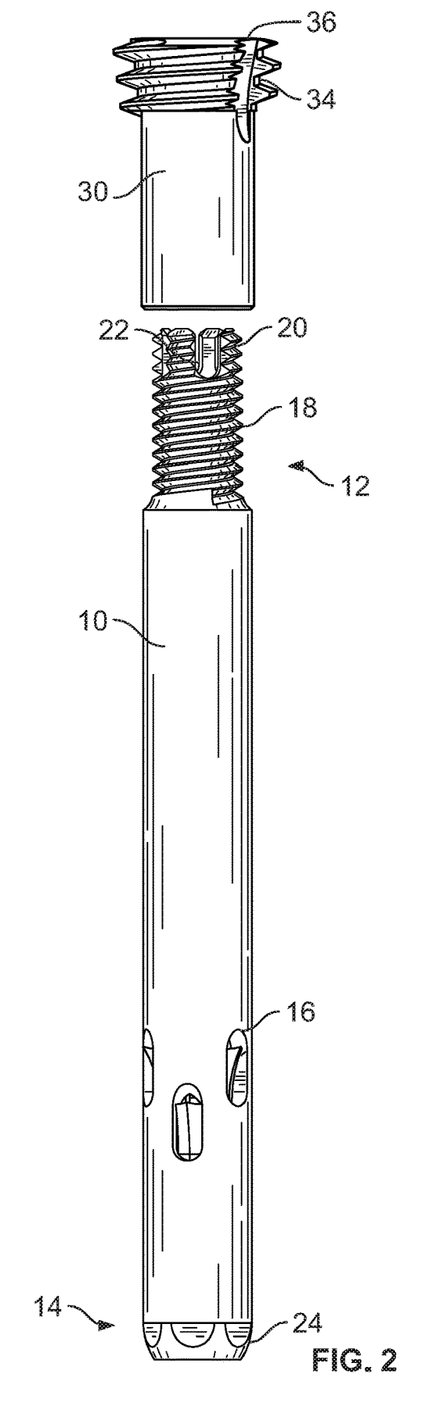
FIG. 2 illustrates a front view of the cannulated compression device.
Figure 3:
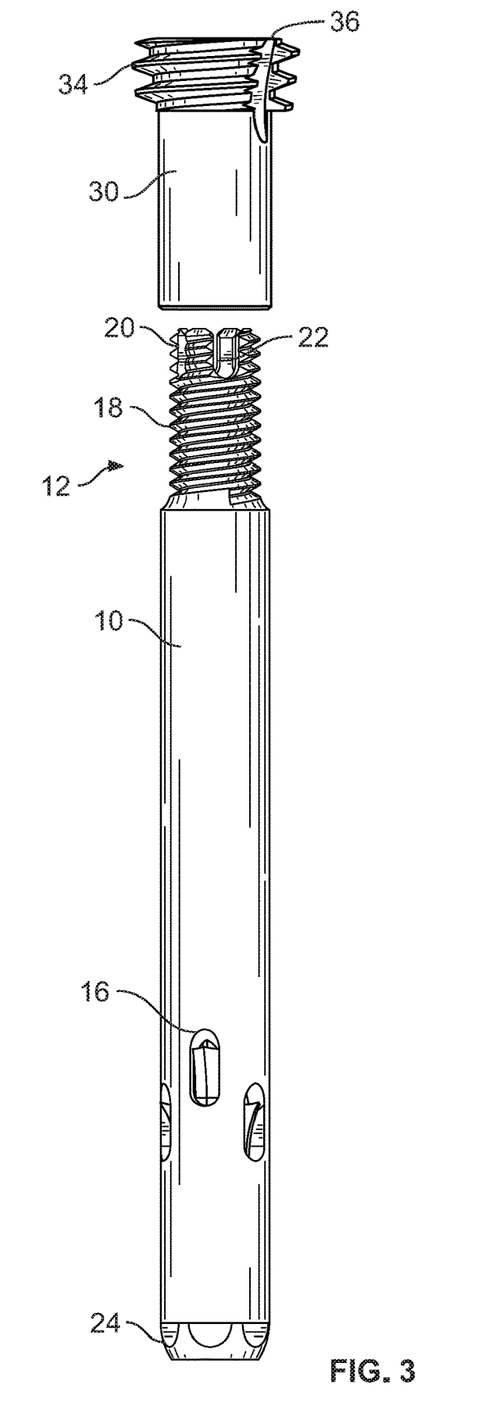
FIG. 3 illustrates a back view of the cannulated compression device.
Figure 4:
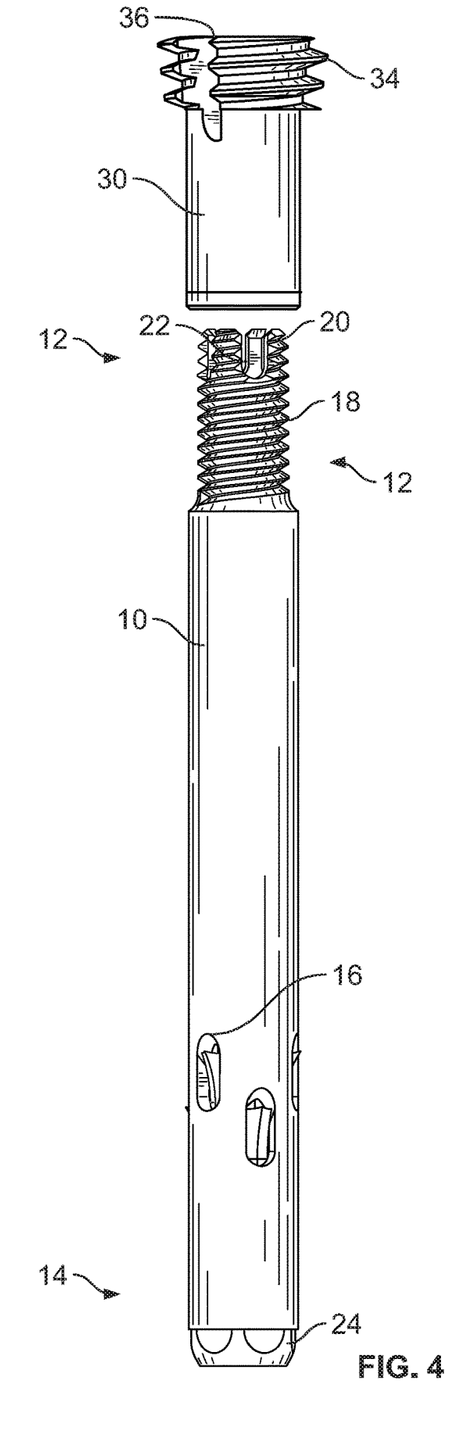
FIG. 4 illustrates a right view of the cannulated compression device.
Figure 5:
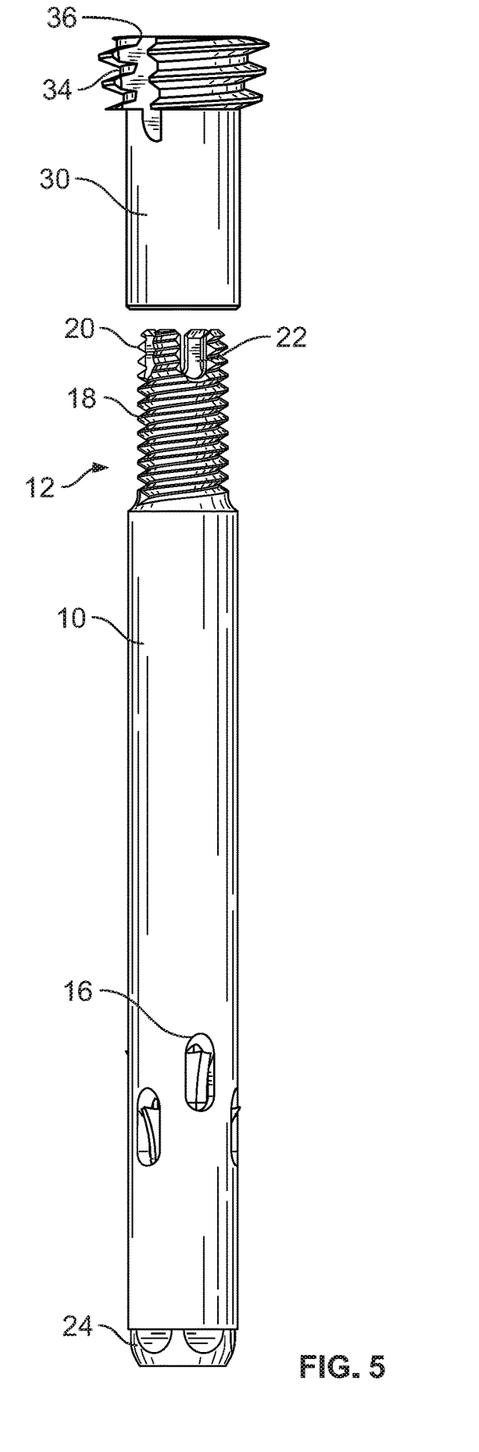
FIG. 5 illustrates a left view of the cannulated compression device.

Referring to FIG. 1, a first isometric view of the cannulated compression device is shown.

The cannulated compression device 1 is shown formed primarily of the tang housing 10 and compression nut 30.

The tang housing 10 includes a proximal end 12 and distal end 14, with tang portals 16.

The proximal end 12 includes tang housing threads 18 that interface with the first set of nut threads 32 of the compression nut 30.

The tang housing threads 18 end in locking fingers 20 with locking gaps 22. The locking fingers 98 of the insertion tool 92 (see FIG. 10) interface with the locking gaps 22 during placement of the cannulated compression device 1, preventing rotation of the tang housing 10.

The distal end 14 of the tang housing 10 includes an end plug 24, with plug bore 26. The cannulated compression device 1 is hollow through its center—cannulated—allowing it to be passed over a guide wire.

The compression nut 30 includes a first set of nut threads 32, shown as internal threads, and a second set of nut threads 34, shown as external threads. One or more cutting grooves 36 help the second set of nut threads 36 to begin threading into the bone 100 (see FIG. 11).

Referring to FIGS. 2-5, multiple views of the cannulated compression device are shown.

The tang housing 10 includes a proximal end 12 and distal end 14, with tang portals 16 and end plug 24.

Tang housing threads 18 include locking fingers 20 separated by locking gaps 22.

The compression nut 30 includes a second set of nut threads 34 with cutting groove 36.

Figure 6:
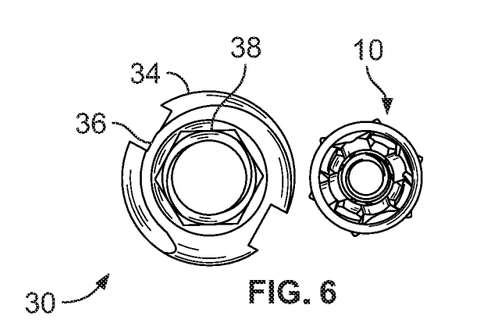
FIG. 6 illustrates a proximal view of the cannulated compression device.

Referring to FIG. 6, a proximal view of the cannulated compression device is shown.

The compression nut 30 is shown with the second set of nut threads 34 on the outside, separated by cutting groove 36.

The internal flats 38 are shown, which are used during installation for interfacing with the compression nut driver 70, specifically the external flats 76 (see FIG. 10) to rotate the compression nut 30.

The tang housing 10 is also shown.

Figure 7:
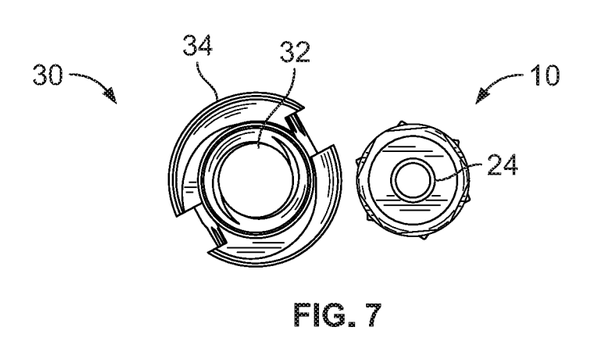
FIG. 7 illustrates a distal view of the cannulated compression device.

Referring to FIG. 7, a distal view of the cannulated compression device is shown.

The compression nut 30 includes both a first set of nut threads 32 and a second set of nut threads 34.

The tang housing 10 is shown with end plug 24.

Figure 8:
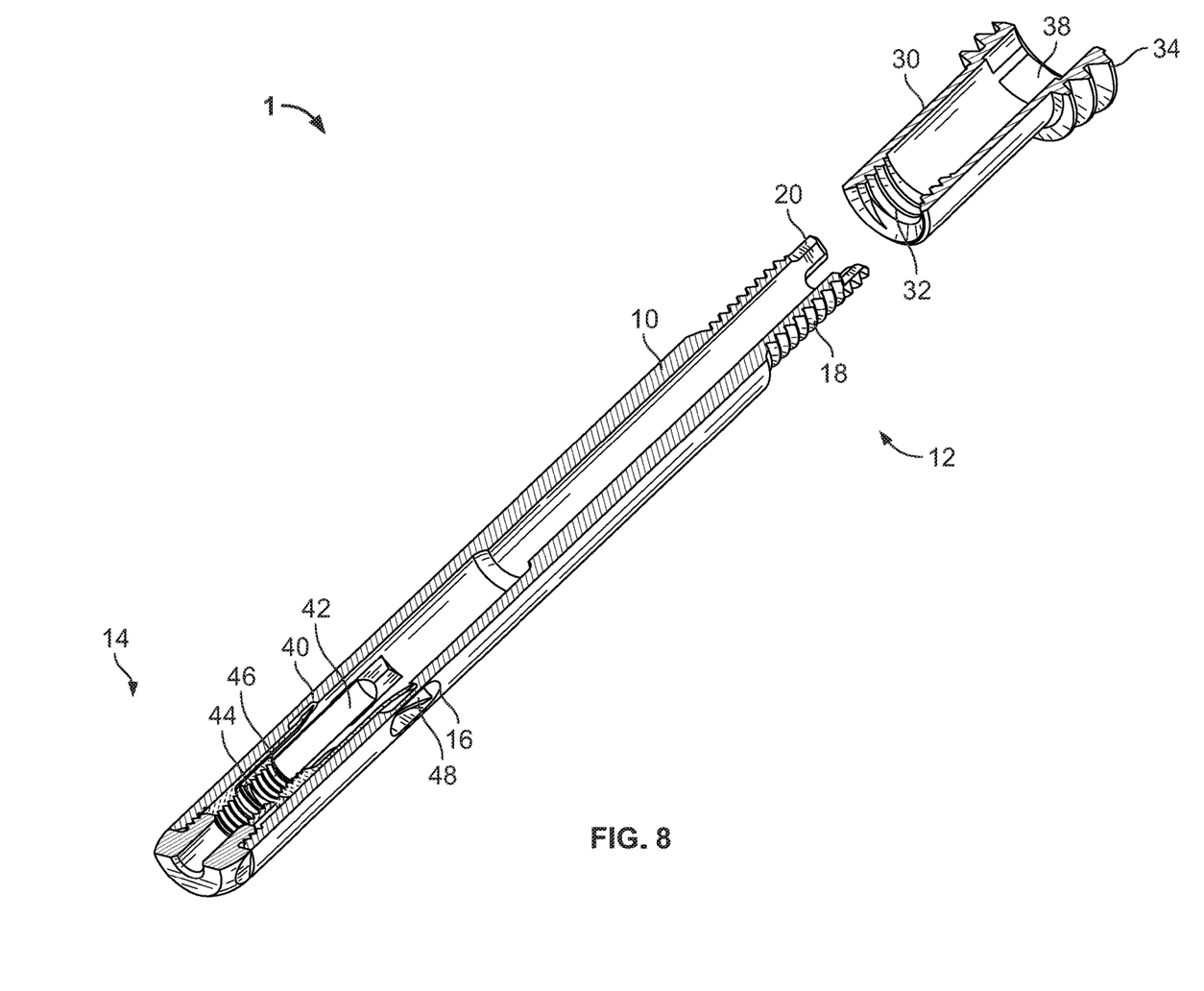
FIG. 8 illustrates a cross-sectional view with tangs retracted of the cannulated compression device.
Figure 9:
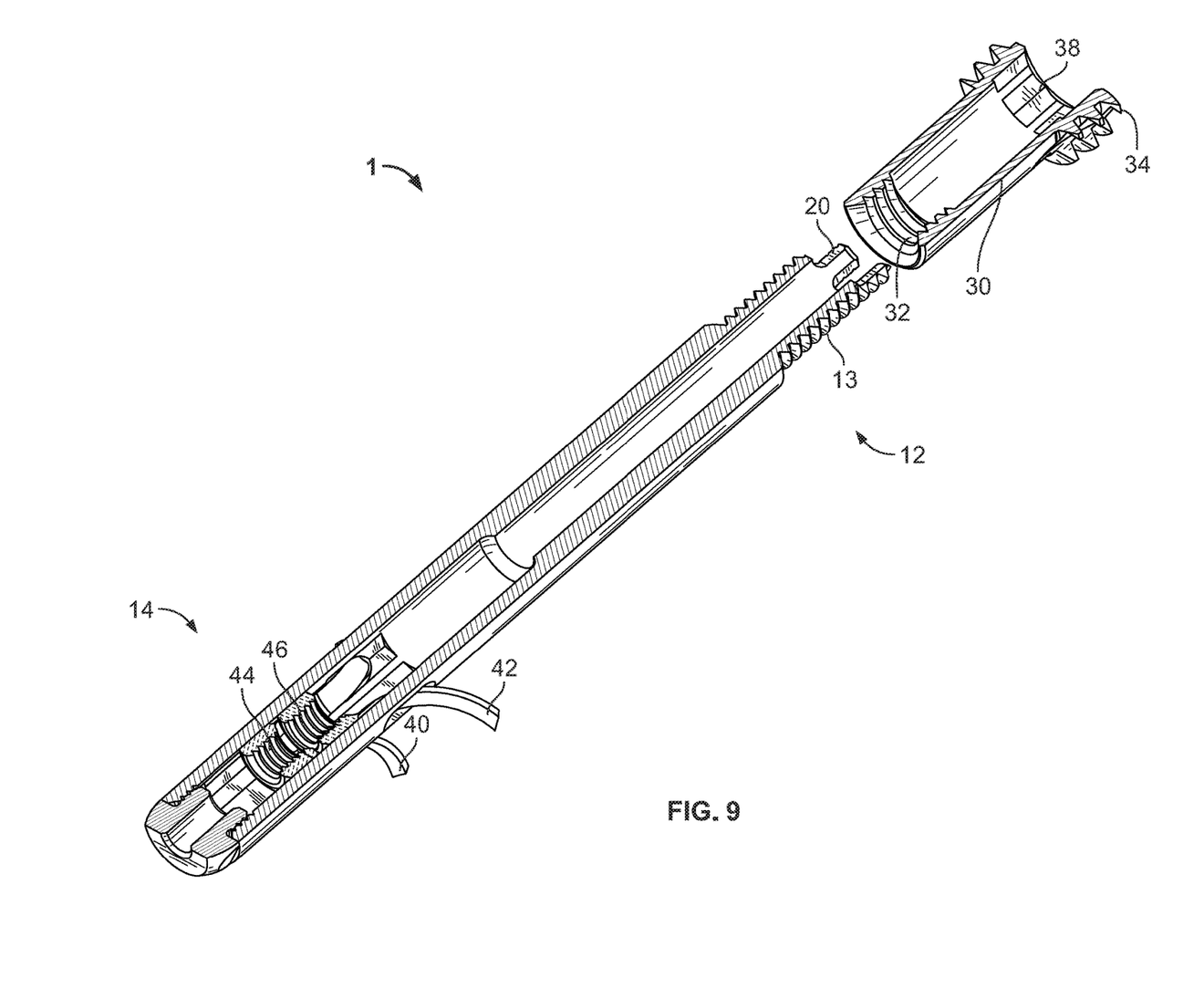
FIG. 9 illustrates a cross-sectional view with tangs extended of the cannulated compression device.

Referring to FIGS. 8 and 9, cross-sectional views with tangs retracted, and tangs extended, of the cannulated compression device are shown.

The tang housing 10 includes tang portals 16, through which the proximal tangs 40 and distal tangs 42 exit when extended. The retracted position of the proximal nail tang threaded hub 44 and distal nail tang threaded hub 46 is near the distal end 14, with the extended position moving the proximal nail tang threaded hub 44 and distal nail tang threaded hub 46 closer to the proximal end The nail tang pre-curved tips 48 sit within the tang portals 16, ready to extend.

The tang housing threads 18, separated by locking fingers 20, interface with the first set of nut threads 32 of the compression nut 30. The second set of nut threads 34 surround the compression nut 30, to interface with the bone.

Also shown are internal flats 38.

Figure 10:
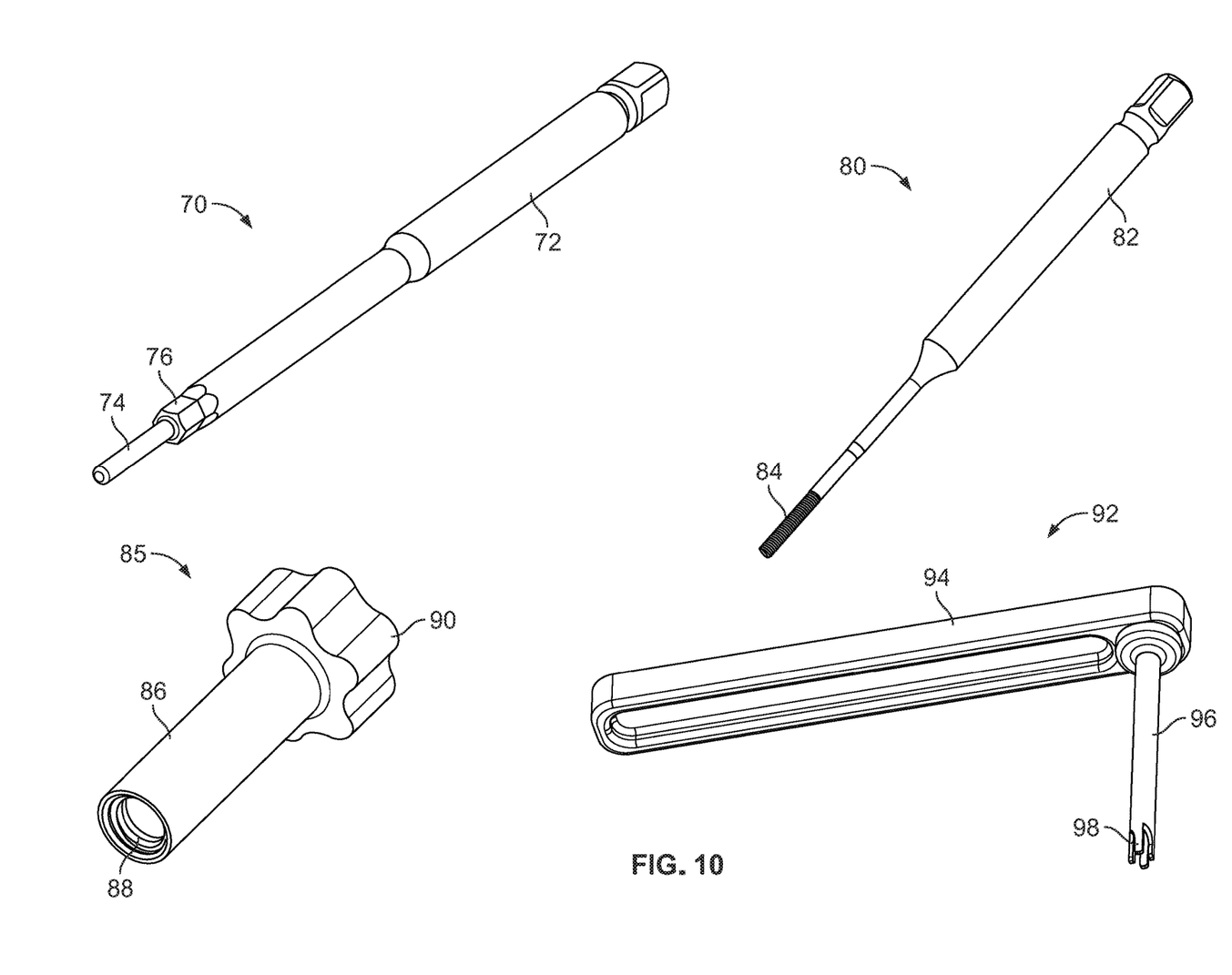
FIG. 10 illustrates tools used for installation of the cannulated compression device.

Referring to FIG. 10, tools used for installation of the cannulated compression device are shown.

The compression nut driver 70 includes a handle 72, with a centering protrusion 74 for insertion into the cannulated compression device 1, the external flats 76 interfacing with the internal flats 38 of the compression nut 30 (see FIGS. 8 and 9).

The tang deployment tool 80 includes a handle 82 and threaded interface 84, the threaded interface 84 interacting with the proximal nail tang threaded hub 44 and distal nail tang threaded hub 46 (see FIGS. 8 and 9).

The compression nut interface tool 85 includes a compression sleeve 86 with internal threads 88. The internal threads 88 interact with the second set of nut threads 34 of the compression nut 30 (see FIGS. 8 and 9). The user grips stabilization ribs 90 to rotate the tool.

The insertion tool 92 includes a handle 94, from which protrudes a hollow extension 96 with locking fingers 98. The locking fingers 98 interface with the locking fingers 20 and locking gaps 22 of the tang housing 10, preventing rotation (see FIGS. 8 and 9).

Figure 11:
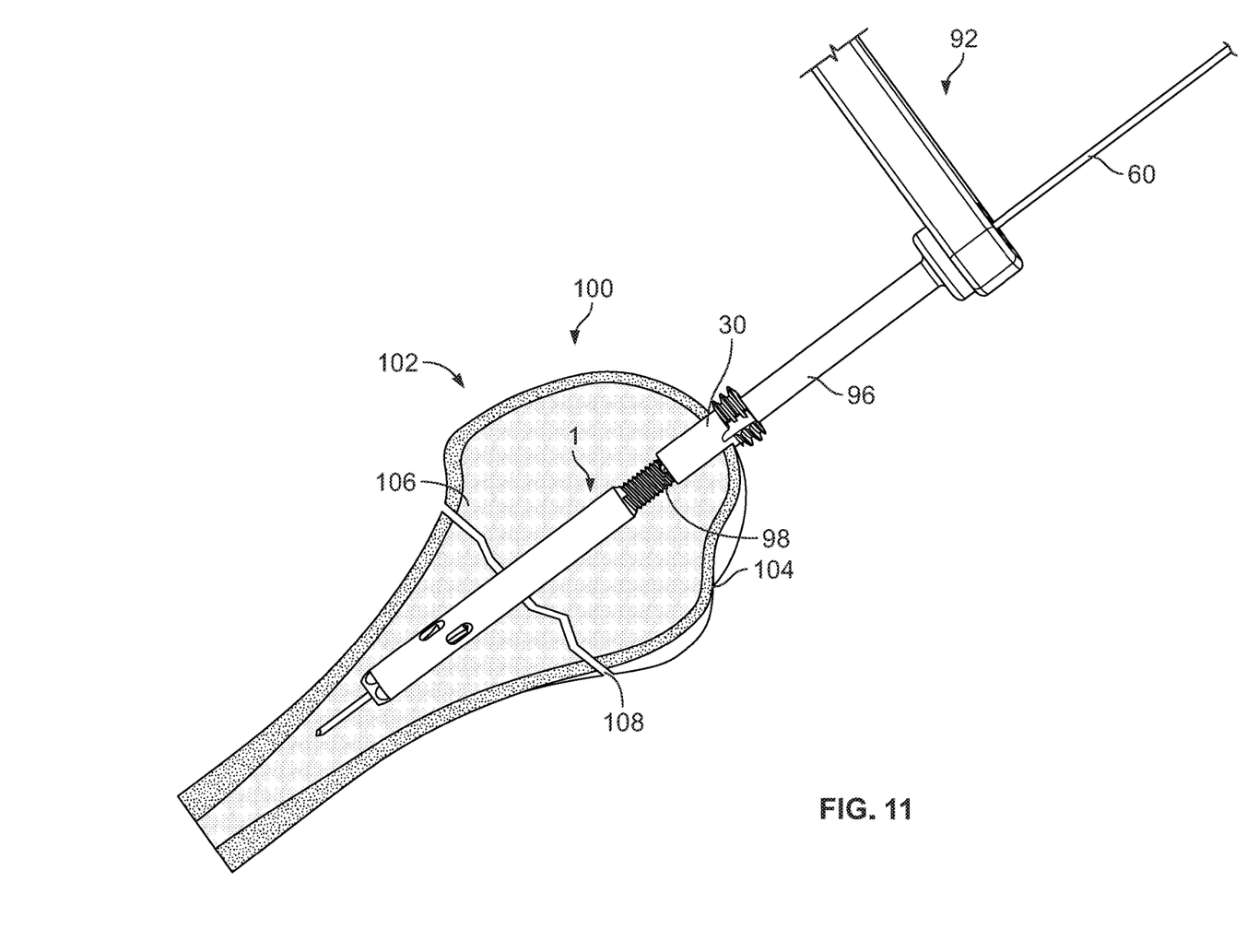
FIG. 11 illustrates the first primary step of installation of the cannulated compression device.

Referring to FIG. 11, the first primary step of installation of the cannulated compression device is shown.

The cannulated compression device 1 was inserted over the guide pin 60, the insertion tool 92 used to press the cannulated compression device 1 into position. The locking fingers 98 of the hollow extension 96 allow insertion without undesired rotation.

The bone 100 includes a fractured component 102, and is formed from the layers cortical bone 104 and trabecular bone 106.

The cannulated compression device 1 is placed across a fracture 108 to be closed during placement.

Figure 12:
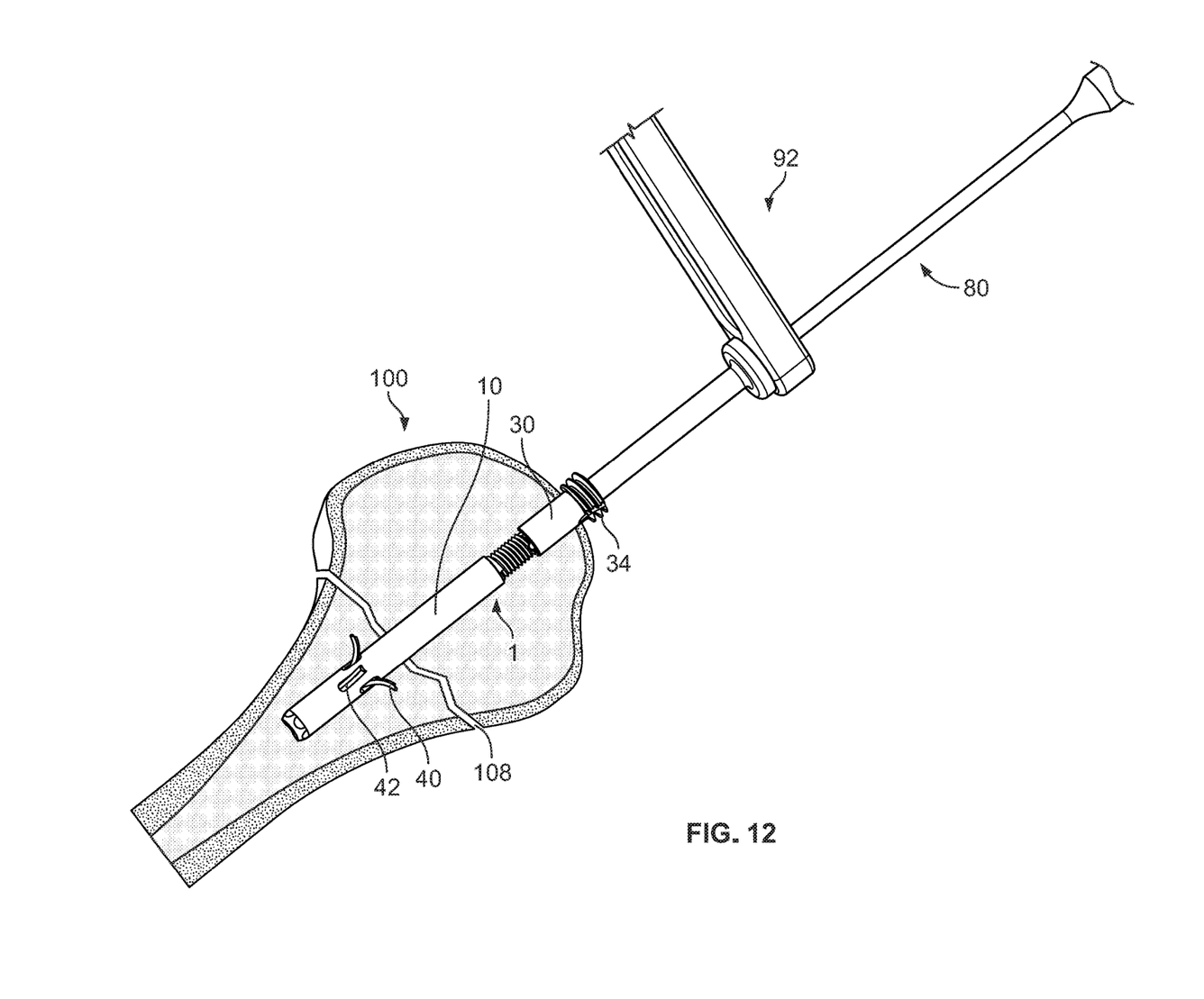
FIG. 12 illustrates the second primary step of installation of the cannulated compression device.

Referring to FIG. 12, the second primary step of installation of the cannulated compression device is shown.

The guide pin 60 (see FIG. 11) is replaced with the tang deployment tool 80. Rotation of the tang deployment tool 80 causes extension of the proximal tangs 40 and distal tangs 42 from the tang housing 10 and into the softer trabecular bone 106. The cannulated compression device 1 is now prevented from rotating with respect to the bone 100.

The second set of nut threads 34 of the compression nut 30 are not yet threaded into the bone 100.

The fracture 108 remains open.

Figure 13:
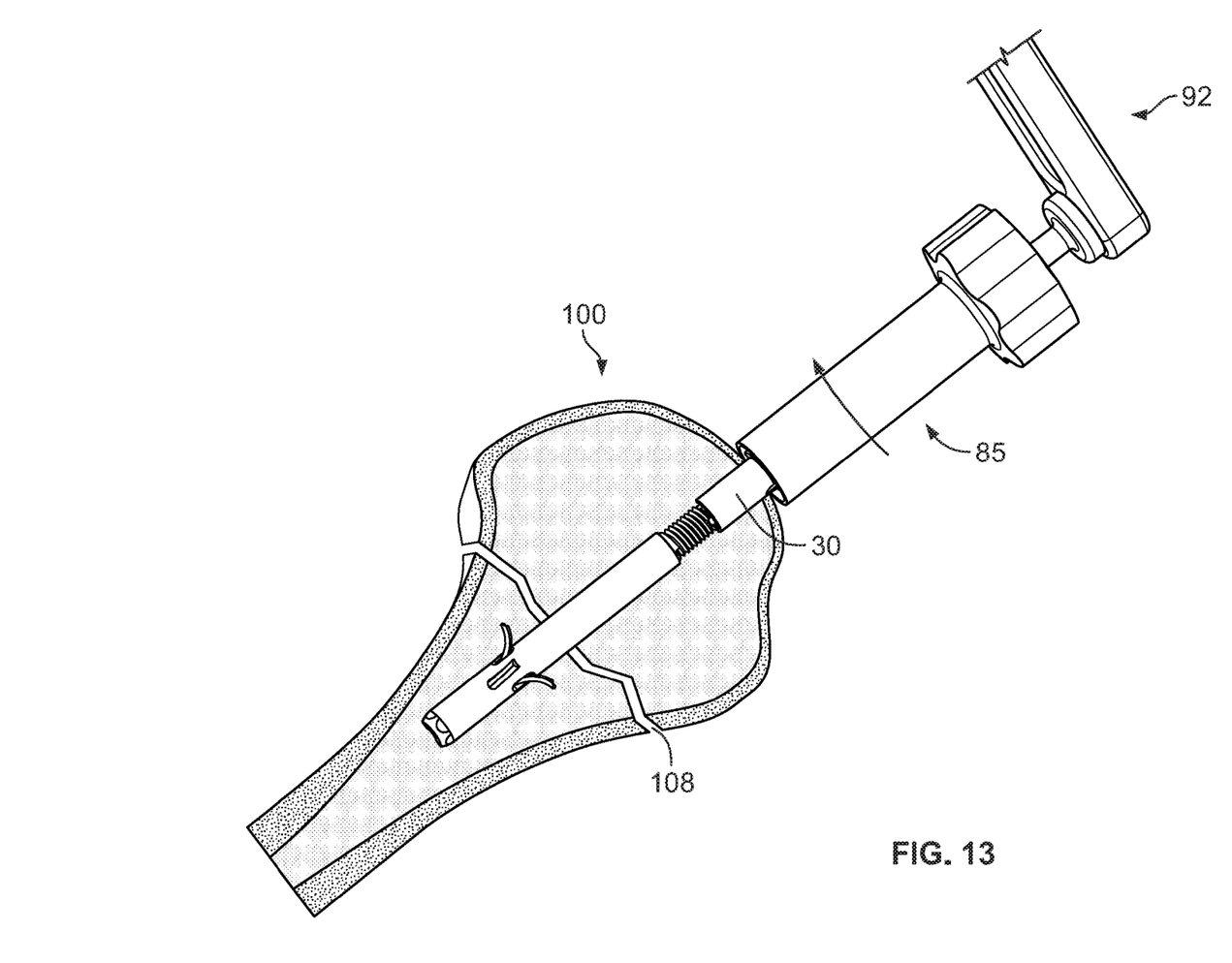
FIG. 13 illustrates the third primary step of installation of the cannulated compression device.

Referring to FIG. 13, the third primary step of installation of the cannulated compression device is shown.

The compression nut interface tool 85 is rotated onto the compression nut 30, seating against the bone 100.

Figure 14:
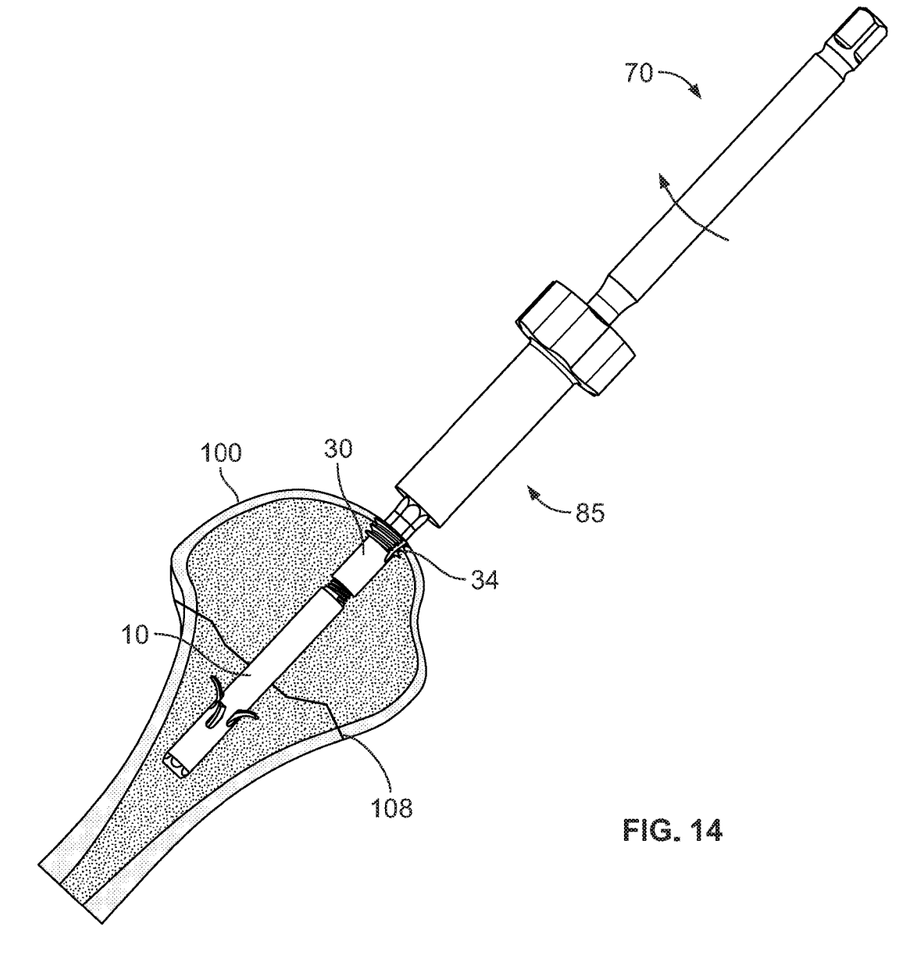
FIG. 14 illustrates the fourth primary step of installation of the cannulated compression device.

Referring to FIG. 14, the fourth primary step of installation of the cannulated compression device is shown.

The compression nut driver 70 is rotated to drive the compression nut 30 into the bone 100. In the process, due to differential threading, the tang housing 10 is drawn toward the compression nut 30, closing the fracture 108.

The compression nut interface tool 85 is shown raised for clarity, but would not be removed until the compression nut 30 is fully threaded into the bone 100.

The tools are then removed, and the surgical site closed.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for fixation of a fracture of a bone, the device to be installed into a hole in the bone, the device comprising:
   a tang housing;
   a nut;
      the nut including a first set of threads and a second set of threads;
      the first set of threads interfacing with the tang housing;
      the second set of threads for interfacing with the hole;
      a single rotation of the nut capable of causing greater linear motion with respect to the tang housing than with respect to the bone;
   tangs extendable from the tang housing;
      the tangs capable of affixing the tang housing with respect to the bone to prevent rotation and linear movement of the device with respect to the bone;
      the tangs extended from an internal position to an external position by a tang extension tool;
         wherein during installation of the device, the tang extension tool is passed through the device to threadably interface with the tangs, the tang extension tool removed after the tangs have reached the external position;
   whereby differential linear motion of the nut, in combination with anti-rotation properties of the tangs, act to close the fracture of the bone.

2. The device of claim 1, wherein:
   the first set of threads is on an internal surface of the nut; and
   the second set of threads is on an external surface of the nut.

3. The device of claim 1, wherein:
   the first set of threads has a pitch greater than that of the second set of threads;
   whereby the single rotation of the nut is capable of causing greater linear motion with respect to the tang housing than with respect to the bone.

4. The device of claim 1, wherein:
   the first set of threads has a pitch less than that of the second set of threads;
   the first set of threads is a double-lead arrangement, where the nut advances two threads per rotation;
   whereby a single rotation of the nut is capable of causing greater linear motion with respect to the tang housing than with respect to the bone.

5. The device of claim 1, wherein:
   the tang housing includes a proximal threaded end;
      the proximal threaded end interfacing with the first set of threads of the nut;
   whereby rotation of the nut with respect to the tang housing causes linear motion of the nut with respect to the tang housing.

6. A device for compressing a bone fracture during installation of the device into a bone, the device for placement across the bone fracture, the device comprising:
   a tang housing;
      tangs extendable from the tang housing;
         the tangs capable of affixing the tang housing with respect to an inside of the bone;
         the tangs extended by a removable tang deployment tool;
            the removable tang deployment tool inserted into the device, rotated, and then removed after tang deployment;
   a nut;
      the nut threadably interfacing with the tang housing;
      the nut capable of threadably interfacing with the bone;
      a rotation of the nut capable of causing greater linear motion with respect to the tang housing than with respect to the bone, to thus pull the tang housing toward the nut, thereby being capable of causing compression of the bone fracture.

7. The device of claim 6, the nut further comprising:
   a first set of threads is on an internal surface of the nut; and
   a second set of threads is on an external surface of the nut.

8. The device of claim 7, wherein:
   the first set of threads has a pitch greater than that of the second set of threads;
   whereby a single rotation of the nut is capable of causing greater linear motion with respect to the tang housing than with respect to the bone.

9. The device of claim 7, wherein:
   the first set of threads has a pitch less than that of the second set of threads;
   the first set of threads is a double-lead arrangement, where the nut advances two threads per rotation;
   whereby a single rotation of the nut is capable of causing greater linear motion with respect to the tang housing than with respect to the bone.

10. The device of claim 7, wherein:
    the tang housing includes a proximal threaded end;
       the proximal threaded end interfacing with the first set of threads of the nut;
    whereby rotation of the nut with respect to the tang housing causes linear motion of the nut with respect to the tang housing.

11. A device for closing a bone fracture during installation, the device comprising:
    a tang housing formed from a first component and a second component;
       the first component removably joined to the second component such that a user can choose a position of the second component with respect to the first component;
       the second component being a threaded nut;
    distal fixation to hold the first component with respect to a first bone fragment;
    tangs extendable from the first component;
       the tangs capable of affixing the tang housing with respect to an inside of the bone;
       the tangs acting as distal fixation to hold the first component with respect to the first bone fragment;
       the tangs only extendable using a removable tang deployment tool, the removable tang deployment tool interfacing with the tangs during placement of the device, extending the tangs, the tang deployment tool then removed;

proximal fixation to hold the second component with respect to a second bone fragment;
a first set of threads on an internal surface of the threaded nut;
a second set of threads on an external surface of the threaded nut,
the first set of threads having a pitch greater than that of the second set of threads;
whereby a single rotation of the threaded nut is capable of causing greater linear motion with respect to the first component than with respect to the bone;
wherein assembling the first component and second component creates a force, for pushing the first bone fragment toward the second bone fragment, to thereby close the bone fracture.

12. The device of claim 11, wherein:
the first set of threads is a double-lead arrangement, where the nut advances two threads per rotation;
whereby a single rotation of the threaded nut is capable of causing greater linear motion with respect to the first component than with respect to the bone.

* * * * *

UNITED STATES PATENT AND TRADEMARK OFFICE
CERTIFICATE OF CORRECTION

PATENT NO. : 11,344,343 B2
APPLICATION NO. : 16/852817
DATED : May 31, 2022
INVENTOR(S) : Joel Bales and Kyle M. Schweser It is certified that error appears in the above-identified patent and that said Letters Patent is hereby corrected as shown below:

On the Title Page

Item (72), delete:
"Kyle W. Schweser"
And insert:
--Kyle M. Schweser--

Signed and Sealed this
Twenty-fourth Day of September, 2024

Katherine Kelly Vidal
*Director of the United States Patent and Trademark Office*